United States Patent [19]
Shields et al.

[11] Patent Number: 5,786,894
[45] Date of Patent: Jul. 28, 1998

[54] MEASUREMENT OF PAPER PULP AND FIBER VISUAL CHARACTERISTICS

[75] Inventors: William R. Shields, Newburgh, N.Y.; Kapil M. Singh, Erie, Pa.; James F. Suska, West Milford, N.J.; Jody MacDonald, Dryden, Me.

[73] Assignee: International Paper Company, Purchase, N.Y.

[21] Appl. No.: 738,161

[22] Filed: Oct. 25, 1996

[51] Int. Cl.$^6$ .......................... G01N 15/02; G01N 21/00
[52] U.S. Cl. .......................... 356/338; 356/343; 250/574
[58] Field of Search .......................... 356/335–343, 356/73, 383, 384, 36

[56] References Cited

U.S. PATENT DOCUMENTS

| | | | |
|---|---|---|---|
| 3,830,969 | 8/1974 | Hofstein | 356/335 |
| 4,804,267 | 2/1989 | Greenfield | 356/335 |
| 5,159,642 | 10/1992 | Kosaka | 382/6 |
| 5,247,339 | 9/1993 | Ogino | 356/73 |
| 5,311,290 | 5/1994 | Olson et al. | 356/383 |
| 5,351,118 | 9/1994 | Spinell | 356/72 |
| 5,495,333 | 2/1996 | Konda et al. | 356/339 |
| 5,570,181 | 10/1996 | Yasuo et al. | 356/336 |

OTHER PUBLICATIONS

Sugden, E.A.N., "A Semi-Automated Method for the Determination of Average Fiber Length Determination by Projection", Pulp and Paper Magazine of Canada, vol. 69, No. 22, pp. 71–76, 1968.

Hill, J., "Pulp Properties to be Measured for Process Control Purposes", Swedish Pulp and Paper Mission, pp. 496–515.

Ory, J. M., and Janin, G., and Thiercelin, F., "Measure Automatique de la Longeur Des Fibres A L'Aide de L-Appareil": Histofibre, Revue ATIP, vol. 43, No. 9, pp. 451–453, Nov., 1989 (French).

Dion, J. L., et al, "Acousto–Optical Fiber Characterization", Tappi Journal, pp. 171–173, Aug. 1989.

Forgacs, O. L., Robertson, A. A. Mason, S. G., "The Hydrodynamic Behaviour of Paper–Making Fibres", Pulp and Paper of Canada, pp. 272–283, May 1958.

Tam Doo, P.A., and Kerekes, R. J., "The Flexibility of Wet Pulp Fibres", Pulp and Paper of Canada, pp. T37–T41 Canada 83:2 (1982).

(List continued on next page.)

*Primary Examiner*—Hoa Q. Pham
*Attorney, Agent, or Firm*—Luedeka, Neely & Graham, P.C.

[57] ABSTRACT

A system for determining characteristics of objects in wood pulp includes a pulp sampling and dilution system for diluting and dispersing samples of pulp, and an imaging/analysis system for capturing images of pulp objects, including fibers, and analyzing the captured images. Samples of pulp are provided to a dispersion tank where pulp is dispersed within a liquid to form a wood pulp slurry having a consistency in the range of from about 0.01 to about 0.001 percent. The dispersed pulp is conducted to a transparent flow cell for imaging and analysis of pulp objects. Light radiating from a light source is reflected off surfaces of objects within the dispersed pulp, producing scattered light. One or more cameras capture scattered light from objects as the objects pass through a camera's field of view. The output of the cameras are digitized and filtered to eliminate motion blur, and the filtered visual image displayed on a monitor. Each pixel of the image is compared to a graylevel threshold, and pixels meeting the graylevel threshold are converted to objects. Object pixels are averaged and compared to a critical mean graylevel threshold. If the average does not meet the critical mean, the object is eliminated from further analysis. Objects meeting the critical mean are analyzed using various size and shape filters to determine properties of the objects. The measured object properties are then displayed on the computer monitor with operator selectable parameters as well as stored in archival files and spreadsheet files, and periodically reviewed by machine operators to enable proper adjustment of process variables.

22 Claims, 9 Drawing Sheets

OTHER PUBLICATIONS

Steadman, R. K., and Luner, P., "The Effect of Wet Fibre Flexibility on Sheet Apparent Density", Proc. of the Fundamentals of Papermaking, Cambridge, 1984.

Kuhn, D.C.S., Lu, X., Olson, J., and Robertson, G., "A Multi-Fiber Method for Measuring Fiber Flexibility", 1994 International Progress in Paper Physics—A Seminar, Aug. 1994.

Seth, R., "The Importance of Fibre Coarseness for Pulp Properties", the Proc. of the Canadian Pulp and Paper Assoc., Jan. 1991.

Clarke, B. Ebeling, K. I., Kropholler, H.W., "fibre Coarseness: A New Method for its Characterization", Paperi ja puuo—Papper och Tra, vol. 67, pp. 490–499, No. 9, 1985.

Jordan, B., Nguyen, N. G. And Page, D.H., "A Image Analysis Procedure for Pulp Coarseness Determinations":, Paperi ja Puu—Pager och Tra, pp. 691–701, No. 11, 1982.

Jordan, B. D., and Page, D.H., "Application of Image Analysis to Pulp Fibre Characterization", Seventh Fundamental Research Symposium, Transactions of the Symposium on the Role of Fundamental Research in Papermaking, Sep. 1981, Cambridge, vol. 2, pp. 745–766, Mech., Eng. Publ. Ltd Ondon, 1983.

Howard, R. C., "Contact Ratio as a Measure of the Bonding Potential of Fibers", STFI Progress in Paper Physics Seminar, Stockholm, p. 166, Jun. 1984.

Sabourin, M., Basrrette, M., Cort, B. J., and Ayer, J., "Benefits of On-Line Fiber Length and Width Index Measurement", submitted for publication to Canadian Pulp and Paper Association reviewed by K. Singh on May 15, 1995.

Hanseler, J., and McKean, W., "Laser Technology Offers New Way to Measure Furnish Components ", Pulp and Paper Canada vol. 89, No. 9, pp. 25–32 (1988).

Glowacki, J.J., "New Cost-Effective Technology Provides Reliable Grayscale Analysis, Objective Results, Improved Scanning Speed, and Operator Ease-of-Use", Pulp and Paper Canada, Feb. 1995, pp. 93–94.

"Optical Characteristics, Dirt, and Shives", pp. 615–638, Controls and Analysis.

"Dynamic Shape Analyzer-10", brochure by Galai Instruments, Inc., 577 Main Street, Inslip, New York 11751.

"Fiber Quality Analyzer", brochure by OpTest Equipment, Inc., 380 Highway 17, Hawkesbury, ON K6A 2R4 Canada.

"FiberScan Fiber Analysis System", brochure by Andritz, Sprout-Bauer.

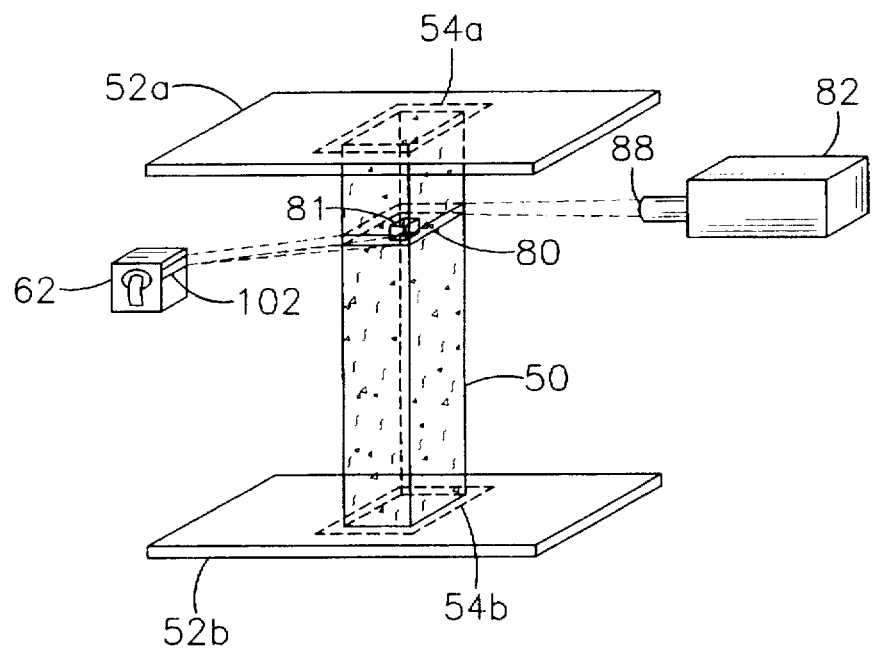
*Fig.* 2A
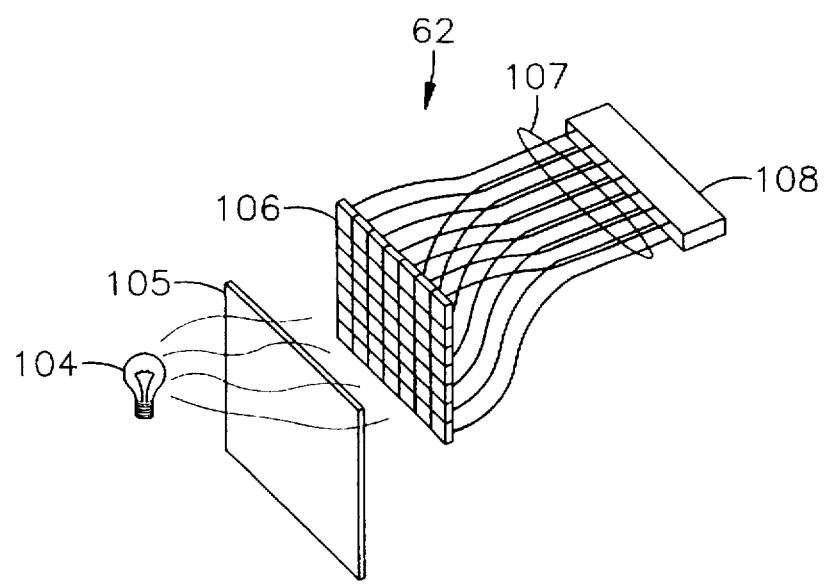
*Fig.* 3

MEASUREMENT OF PAPER PULP AND FIBER VISUAL CHARACTERISTICS

TECHNICAL FIELD

The present invention relates to measurement of wood pulp characteristics and particularly to an on-line method and apparatus for measurement and control of wood pulp characteristics during production.

BACKGROUND

In papermaking operations, wood is subjected to various mechanical and/or chemical processes with the aim of liberating and individualizing fibers from the wood stock, producing what is commonly referred to as wood pulp. The pulp production process is replete with complex and interrelated process variables that can affect pulp and fiber properties, and ultimately paper quality. For example, when wood chips are cooked with chemicals to break down the wood structure to release the fibers and dissolve out the lignin, there is an inevitable loss of fiber strength due to chemical attack on the cellulose molecule. The strength loss is often accompanied by a loss in viscosity and other dimmishments in desirable properties. Mechanical treatments such as refinement, grinding and depressuring or "blowing" also serve to liberate the fibers, but these processes can have undesirable effects leading to fiber curls, excessive fiber length and/or width decrease as well as fiber clusters known as "shives" due to underefining.

The wood pulp slurry produced by a combination of chemical and mechanical treatments is often subjected to a further chemical treatment known as bleaching where the fibers are further delignified and decolored to lighten the fibers for production of white paper. Bleaching also tends to diminish fiber strength and viscosity, as the chemicals will attack the cellulose to some degree.

Once a pulp of the desired degree of delignification (yield) and whiteness is obtained, it is then diluted to a consistency in the neighborhood of a few percent (usually 1–3%) wood fibers in water to make what is known as the furnish. The furnish is then pumped to a headbox and released in the form of a wide, relatively thin jet known as a slice onto a high speed forming wire moving in the slice direction at about the same linear velocity. Water drains through the wire leaving the fibers deposited thereon as a web which then undergoes consolidation and with further downstream processing becomes a paper or board sheet, depending the thickness and other properties of the web and its fiber constituents.

The papermaker will often tailor the fiber make-up of the furnish to produce a paper or board sheet with desired properties by mixing various pulp grades or types of pulp coming into the headbox. Higher quality pulp of certain fiber lengths is often mixed with lower quality pulp having shorter fibers and/or a greater shive content, higher degree of foreign material such as "stickies" or "tackies" or particles which are typically present to some degree in pulp produced from recycled paper, for example. Also, with the advent of multi-slice headboxes and multiple headbox lines for making multi-ply paper and board products, different layers of the resulting sheet of board can be tailored to exhibit different properties by mixing different pulp grades for the furnish used to supply the various headboxes.

Because of the many variables which can be adjusted to alter the web make-up on the forming wire, it is important that the papermaker be able to accurately monitor and control all possible effects of changing the pulp make-up and/or machine operating conditions.

Systems are currently available which enable limited measurement of some pulp and fiber visual properties by use of various flow cells and video imaging techniques. However, many of these systems are available only in laboratory instruments and are not suitable for on-line use with actual pulp streams. In an on-line environment, pulp streams often contain large particles or shives which would block the capillary openings in the flow cells of such instruments.

Existing fiber measurement systems typically employ a single camera viewing a backlighted sample through a sample tube, which severely limits the types and accuracies of fiber characteristics which can be measured. Such systems a camera can be used to determine various characteristics off-line, but they are not effective for obtaining the highly accurate measurements needed for on-line monitoring and control of pulp properties.

Also, in a papermaking facility it is often useful for personnel to know how long a recently discovered characteristic of the pulp and fibers has been present. There are presently no on-line systems which enable plant personnel to monitor pulp properties with substantially continuous, real time data so that appropriate adjustments can be made with immediate observable effects.

Therefore, it is an object of the present invention to provide a method and apparatus for on-line measurement and control of pulp and fiber visual properties where the apparatus and method are fully integratable with the production process.

Another object of the present invention is to provide a fiber imaging apparatus for highly accurate measurement of pulp and fiber visual properties.

Another object of the present invention is to provide a fiber imaging and measurement apparatus which improves measurement accuracy by measuring only the most clearly imaged fibers available.

Another object of the present invention is to provide a fiber imaging and measurement apparatus which provides multiple angle and multiple magnification level imaging of fibers.

Another object of the present invention is to provide an on-line pulp and fiber measurement apparatus which enables a user of the apparatus to graphically display measured fiber properties to plant personnel.

Another object of the present invention is to provide a pulp and fiber measurement apparatus which enables machine operators to access visual properties of fibers which have been measured over an historical period of paper production.

Another object of the present invention is to provide an on-line pulp and fiber measurement apparatus that reduces waste by returning sampled pulp and fibers to the production furnish.

SUMMARY

With regard to the foregoing objects and advantages, the present invention provides a system for determining the characteristics of objects having surfaces, including wood fibers, dirt and shives, in wood pulp. The system includes means for dispersing the pulp in a liquid, such as water, to produce a wood pulp slurry having a consistency in the range of from about 0.01 to 0.001 percent.

The pulp slurry is conducted into a transparent flow cell where a light source positioned adjacent the flow cell radiates light into an illumination area of the cell. Radiated light is reflected off surfaces of objects to produce scattered light. The scattered light is received by a first camera which is positioned substantially orthogonal to the light source and adjacent the flow cell at a first viewing angle to the illumination area. Upon initiation of the first camera, a portion of the scattered light in the first field of view is received by the camera. The first camera produces a first plurality of video signals corresponding to the scattered light.

The video signals are sent to a framegrabber circuit and digitized to produce a first image having a plurality of pixels (picture elements) in two-dimensional alignment. The framegrabber, which also initiates the light source and camera, holds the first image for display and analysis.

The framegrabber circuit is controlled by a digital data processor to initiate the light source and camera to produce the first image. The data processor also controls the framegrabber to output the first image for display and analysis. The data processor analyzes the first image and, based on the results of the analysis of the first image, produces a second image which includes only objects from the first image that have predefined sizes and mean gray-levels. The second image is then analyzed by the data processor to determine one or more characteristics of the objects. A display is provided for visually displaying any combination of the images.

Preferably, the first camera is a charge coupled device camera which produces a first matrix of signals corresponding to the two-dimensional array of pixels of the first image. This type of camera is used in conjunction with a filter which eliminates motion blur from the first image.

Alternatively, the first camera is a non-standard (e.g., non RS-170, full frame array) camera and the light source is a strobed light source. In this alternate first camera embodiment, a Bitflow Raptor framegrabber board is used.

In either embodiment, to produce the second image, the pixels of the first image are analyzed by comparing each pixel to a threshold pixel value. Contiguous pixels that meet the threshold are converted to objects which are filtered to eliminate objects that do not meet predefined size and shape criteria.

A second camera may be added to the system to provide additional images of objects within the pulp slurry, such as the widths of fibers. The second camera is also positioned adjacent the flow cell, but at a second viewing angle where scattered light is received from a second field of view smaller than the first field of view. A second plurality of video signals is produced by the camera and digitized by the framegrabber circuit to produce a third image having a plurality of pixels in a two-dimensional array. As with the first image, the framegrabber circuit holds the third image for display and analysis by the data processor. The data processor analyzes the third image and produces a fourth image corresponding to only the width of a fiber positioned within the second field of view. Fiber width is determined by the data processor.

To improve the accuracy of object characteristic measurements, a third camera may be added to the system to provide multiple angle imaging of objects within the first field of view. The third camera is positioned adjacent the flow cell at a third viewing angle to receive scattered light from the first field of view. Scattered light reflected off objects within the pulp is received by the third camera and a third plurality of video signals is produced and then digitized by the framegrabber to produce a fifth image for display and analysis. The data processor analyzes the fifth image to produce a sixth image corresponding to only fibers positioned within the first field of view. The sixth image is then analyzed to determine one or more fiber characteristics which are compared with fiber characteristics determined from the second image to improve the accuracies of fiber characteristic measurements.

The present invention also provides a method for determining various characteristics of wood fibers found in wood pulp, including fiber length, perimeter, area, and curliness. Wood pulp is dispersed in a liquid to produce a wood pulp slurry having a consistency in the range of about 0.01 to 0.001 percent. The pulp slurry, which contains objects such as wood fibers, is conducted to a transparent flow cell for imaging. Objects within a first field of view of the flow cell are illuminated with a light source and imaged at a first substantially orthogonal viewing angle to the light source, producing a first plurality of video signals containing illuminated objects. The video signals are digitized to produce a first image having a plurality of pixels in a two-dimensional array. The first image is analyzed to produce a second image containing only objects having predefined sizes and shapes that are positioned within the first field of view. One or more object characteristics are then determined from an analysis of the second image.

Based on the object characteristics that are determined by the present invention, the pulp refinement process can be adjusted to optimize characteristics of the pulp slurry.

Analysis of the first image may include comparing each of the pixels to a threshold value. Contiguous pixels that equal or exceed the threshold value are converted to objects which are then filtered to eliminate objects from the image that do not meet predefined sizes and shapes of objects.

BRIEF DESCRIPTION OF THE PREFERRED EMBODIMENTS

The preferred embodiments of the invention will now be described in further detail with reference to the drawings wherein like reference characters designate like or similar elements throughout the several drawings as follows.

Figure 2B:
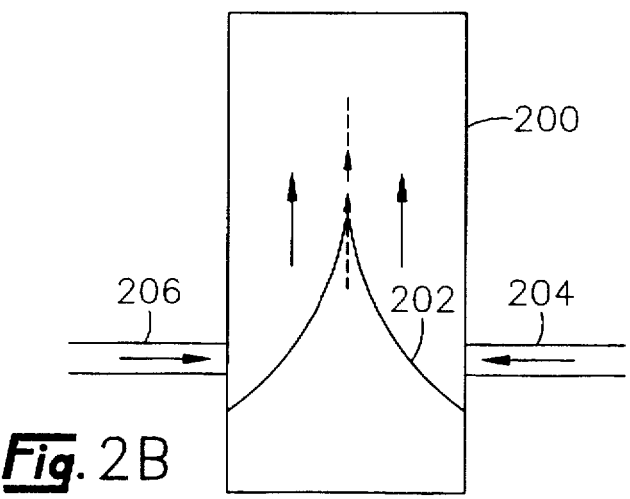
FIG. 2A is an isometric drawing of the imaging flow cell illustrating positions of a lighting system and a primary camera with respect to the flow cell.
Figure 2C:
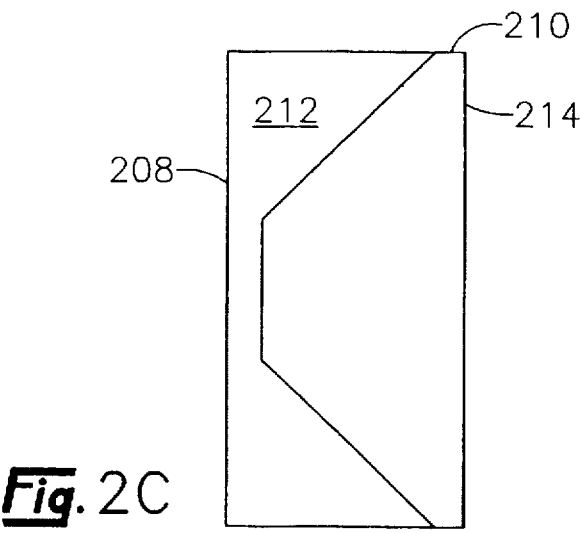
Figure 2D:
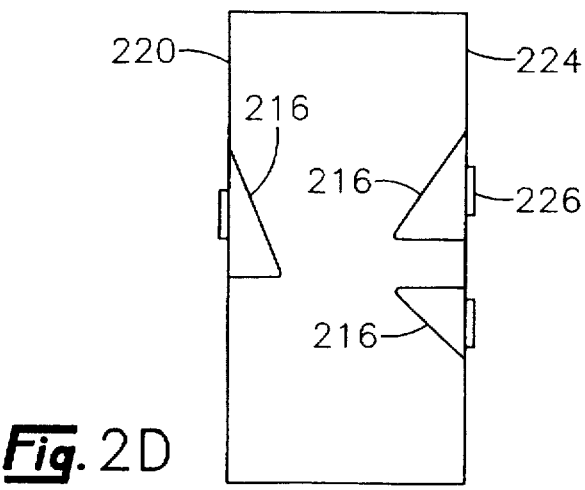
Figure 4:
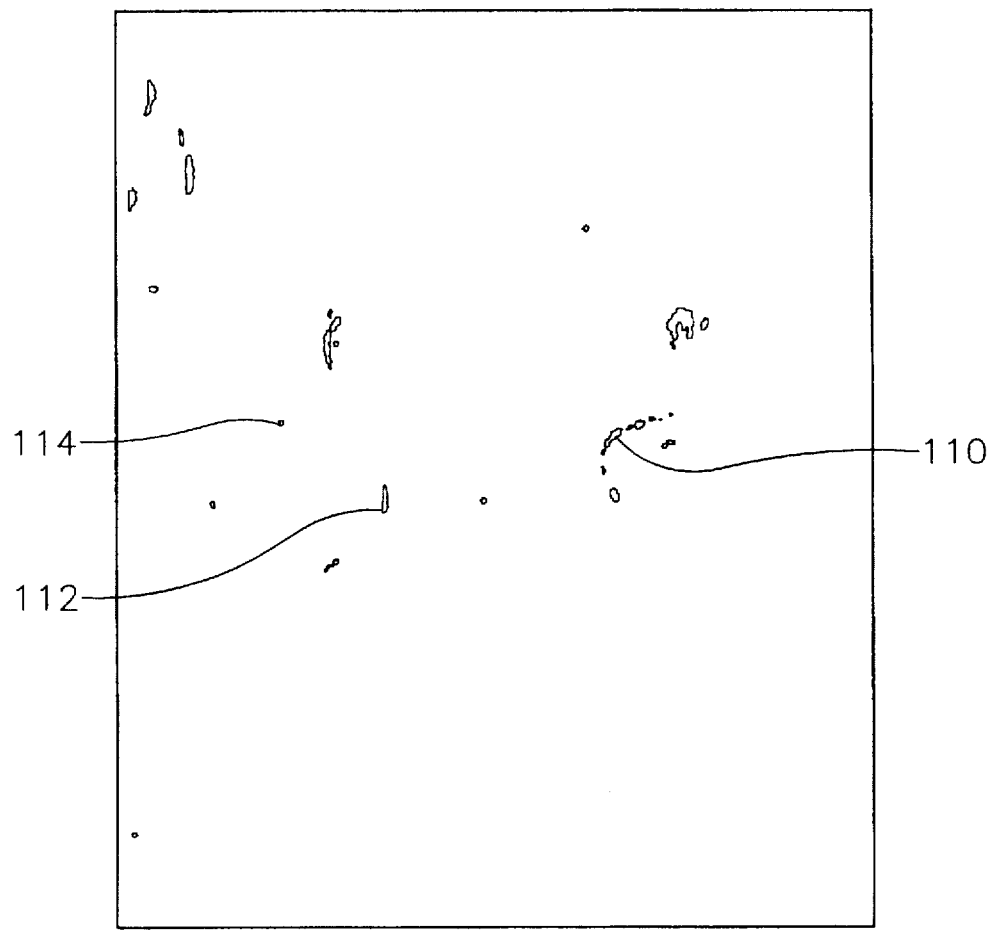
Figure 5:
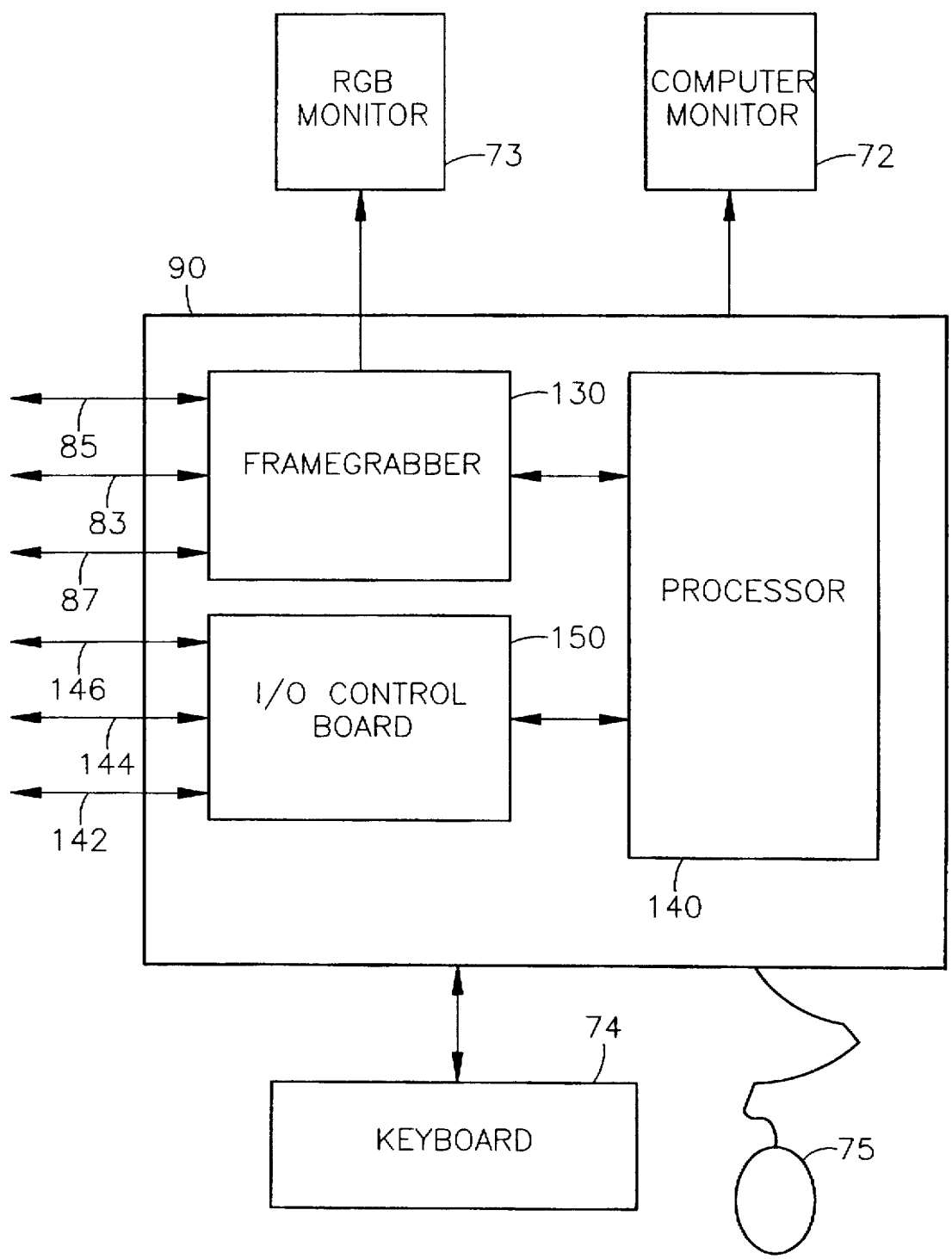
Figure 6:
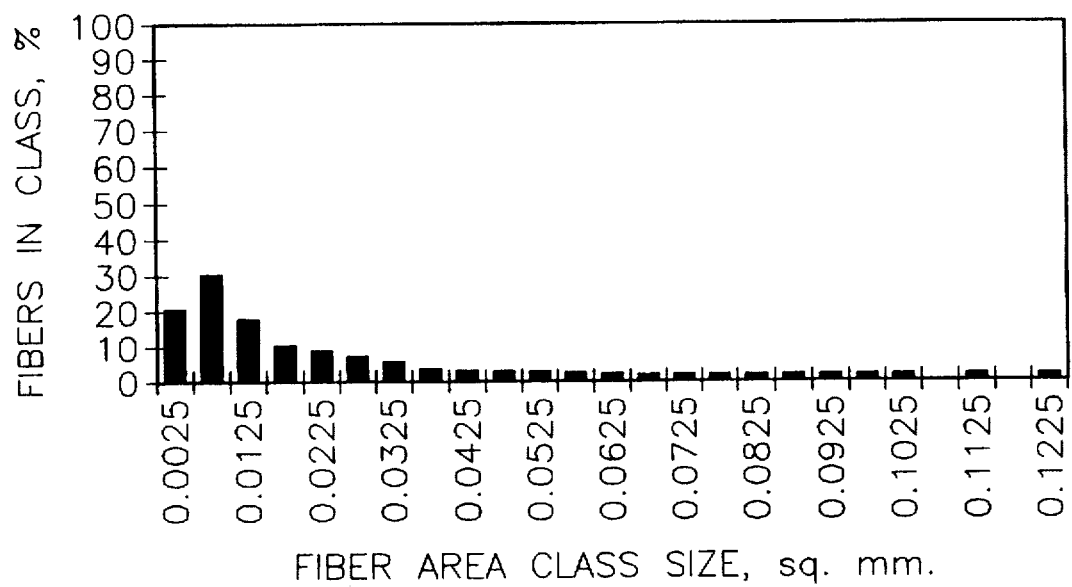
Figure 7A:
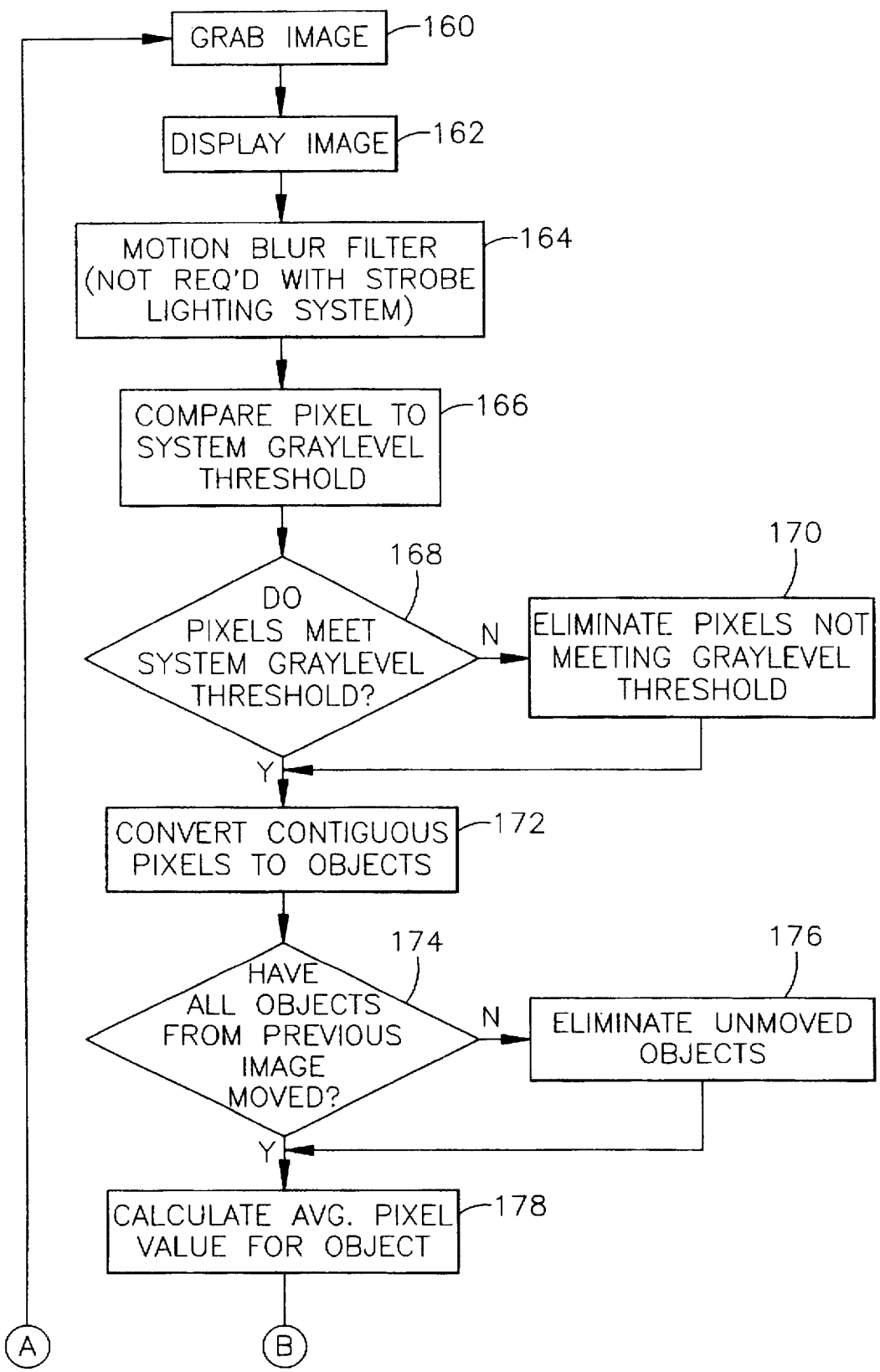
Figure 7B:
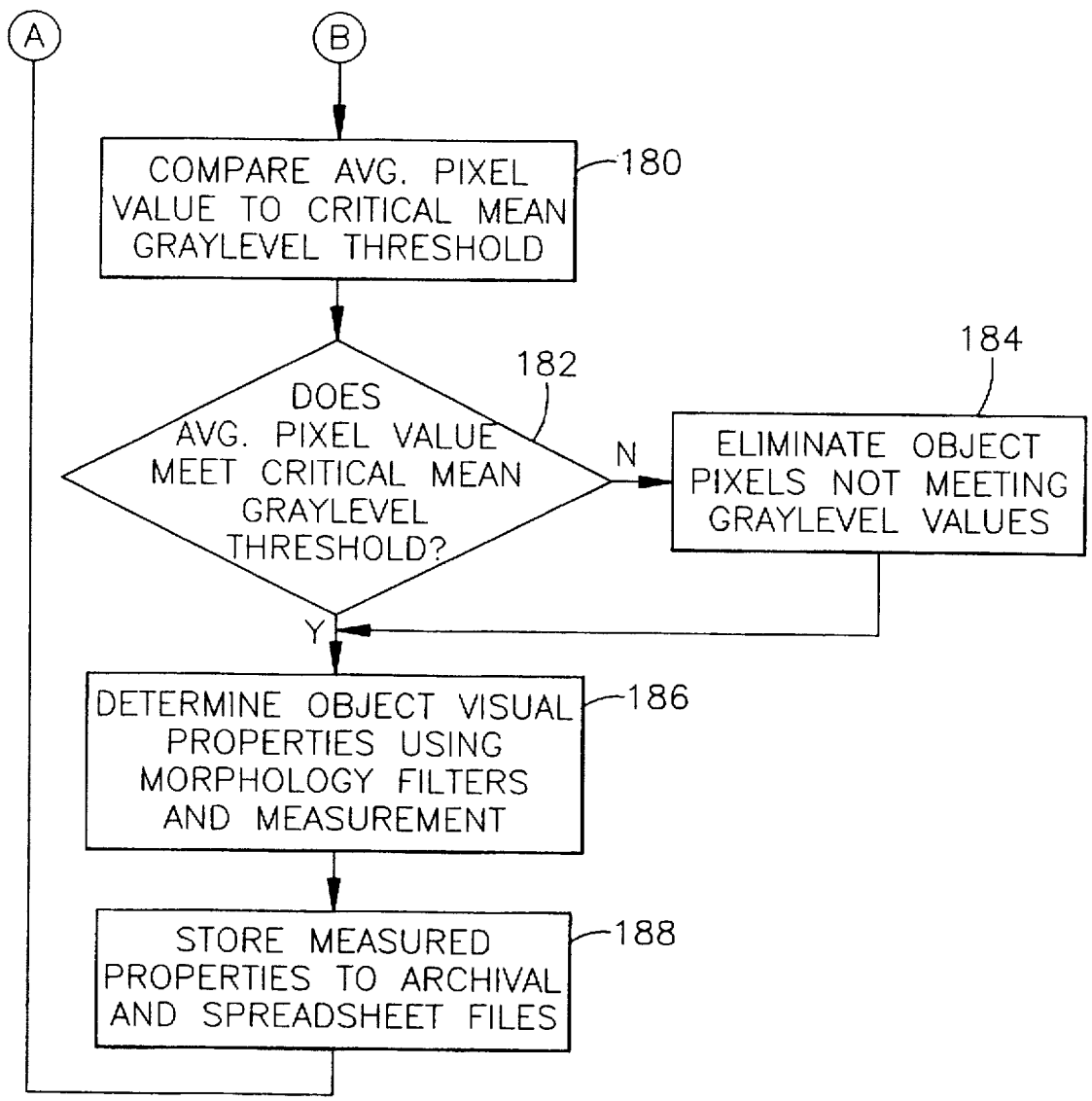
Figure 8:
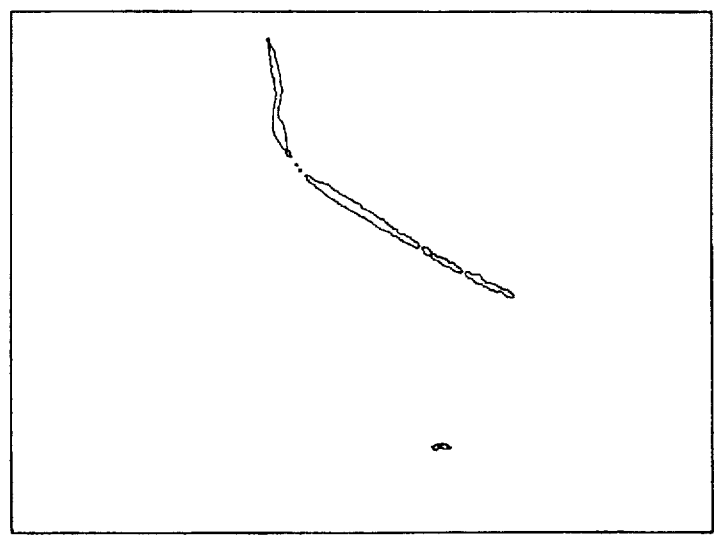

FIGS. 2B–D are side views of three alternate embodiments of the flow cell of FIG. 2A;

FIG. 3 is a drawing of the lighting system;

FIG. 4 is a typical image of various pulp objects as captured by the primary camera with the camera's field of view set for imaging of individual fibers;

FIG. 5 is a functional block diagram of a computer for use in processing data according to the invention;

FIG. 6 is a graph illustrating fiber area measurements;

FIG. 7 is a flowchart of an image acquisition and analysis process according to the invention; and FIG. 8 is a typical image of the end of a fiber as captured by the secondary camera.

DETAILED DESCRIPTION OF PREFERRED EMBODIMENTS

Figure 1:
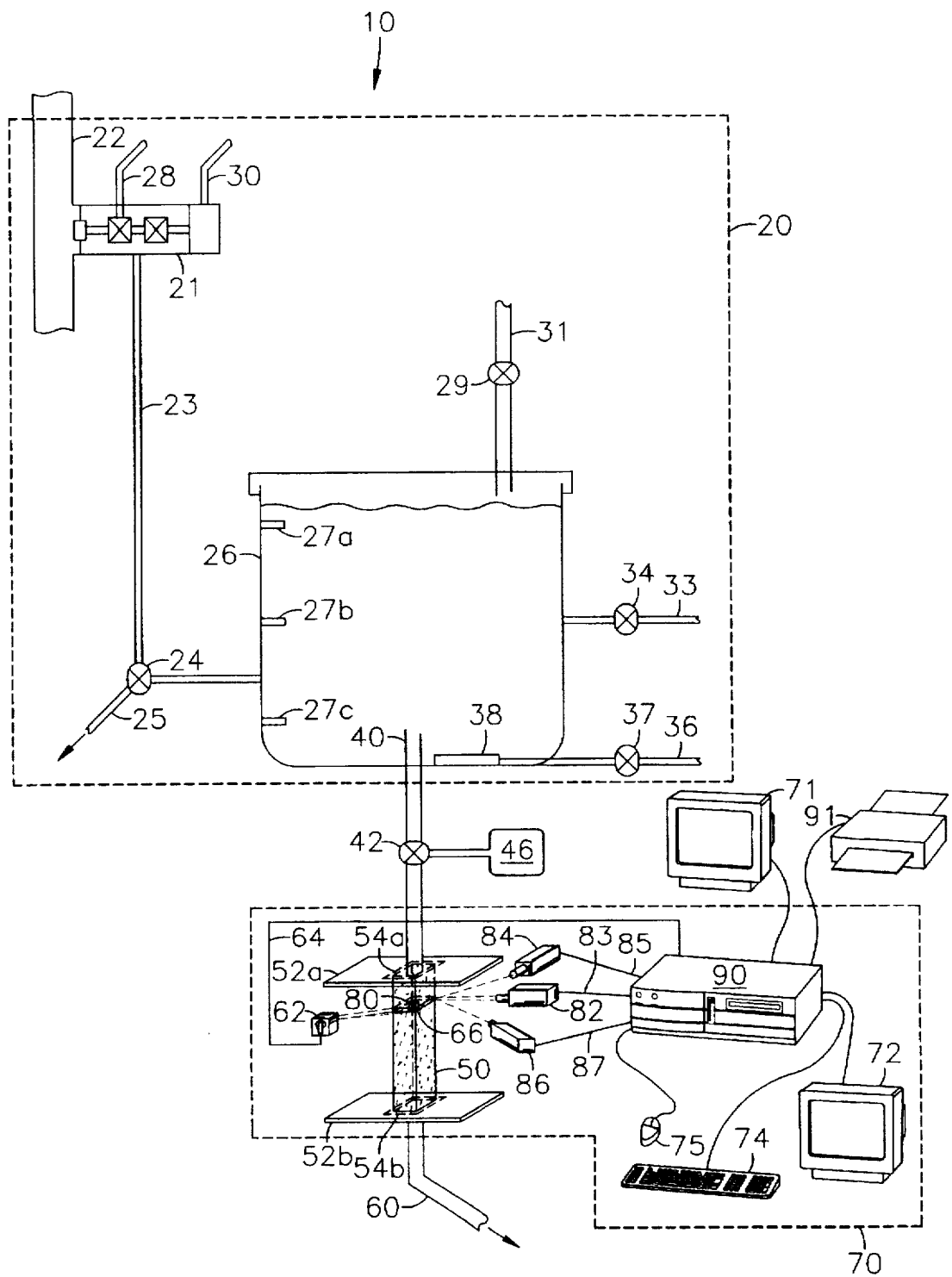
FIG. 1 is a diagrammatical view illustrating aspects of a pulp and fiber visual properties measurement system according to the present invention.

In accordance with a preferred embodiment of the present invention, there is provided in FIG. 1 a pulp visual observation and measurement system 10 for on-line observation, measurement and control of paper pulp properties, including shive content, dirt count, hardwood/softwood content, percentage of long fibers, fines content and characteristics, coarseness, fiber fibrillation, fiber species identification, pulp consistency, and pulp brightness. Generally, the system 10 provides measurements and quantification of these and other visual properties by diverting a sample of pulp from a stream of pulp during the pulp production process, diluting the pulp sample to disperse the pulp fibers and other objects, imaging the dispersed fibers and objects, and measuring the properties of the dispersed objects both visually and analytically. Pulp property measurements and visual observations provided by the system 10 are stored over time and graphically presented during papermaking operations, providing machine operators with on-line process feedback to enable optimization of process variables. Thus, machine operators are able to achieve consistency of desired pulp and fiber properties and hence, to control paper properties.

The pulp visual observation and measurement system 10 is functionally divided into two main parts or subsystems: (1) a pulp sampling/dilution system 20; and (2) an imaging/analysis system 70. The pulp sampling/dilution system 20 functions to individualize and disperse objects within the pulp sample to enable the imaging/analysis system 70 to image objects and determine various object parameters from the images. As FIG. 1 illustrates, the pulp sampling/dilution system 20 consists of a sampler 21 for diverting a sample of pulp from a pulp conduit 22, which carries up to about 5% pulp in solution, into a dilution tank 26. Sampler 21 may be connected at any point along the pulp conduit 22 and at any stage of pulp refinement to divert a sample of pulp for visual observation and analysis. The sampler 21 dilutes the pulp sample to approximately 0.5% pulp in solution by mixing water from line 28 and air from line 30. Flow of diluted pulp from line 23 into the dilution tank 26 is regulated by a valve 24 that is preferably controlled by a computer 90. Three level sensors 27a, 27b, and 27c provide the computer 90 with an indication of the fill level within the tank 26. Excess diluted pulp is sent to recycling via line 25.

Pulp within the dilution tank 26 is further diluted with water from line 33 to achieve a consistency from about 0.01 to 0.001% pulp in solution. A solenoid valve 32, also controlled by computer 90, is used to regulate the flow of water from line 33 to tank 26. Continuous mixing of pulp is provided within the tank 26 by a mixing air bubbler 38 that receives supply air via line 36. A computer controlled valve 37 regulates air supply to the bubbler 38. Output of the dispersed pulp from dilution tank 26 is regulated by valve 42, also controlled by computer 90, via line 40 and supplied to transparent flow cell 50 for imaging and analysis. To adjust flow rate into line 40, a computer controlled valve 29 is used to control the supply of low pressure air from line 31 into the tank 26. When needed, line 31 supplies positive air pressure to the tank 26 to facilitate the flow of dispersed pulp from the tank 26 and into line 40.

In a preferred embodiment, flow cell 50 is a one inch square by eight inch long flow cell, enabling even large shives to pass through without clogging. After passing through flow cell 50, the diluted pulp sample enters line 60 where it is supplied to recycling. Although the preferred embodiment of FIG. 1 illustrates supply of pulp to the flow cell 50 by gravity feed and/or air pressure, it will be understood that the dispersed pulp exiting dilution tank 26 may be supplied to flow cell 50 by pump means (not shown).

Other flow cell configurations, such as those shown in FIGS. 2B through 2D, are also utilized. The flow cell 200 of FIG. 2B includes a funnel 202 into which dilute pulp is received. Water, or other liquid, is introduced to the flow cell 200 by lines 204 and 206 immediately above the funnel 202 as shown. Water flow, indicated generally by arrows, creates a vortex at or near the tip of the funnel 202 which produces a relatively narrow, defined stream of dilute pulp which can be imaged as pulp exits the tip of the funnel 202. In the flow cell 208 of FIG. 2C, dilute pulp enters the flow cell 208 at a relatively narrow opening 210 between a block 212 positioned within the flow cell 208 and the flow cell wall 214. Objects within the pulp are impaged as the objects drift within the flow cell 208. In FIG. 2D, a plurality of islands 216 are positioned within the flow cell 220 as desired. The islands 216 are attached to the flow cell wall 224 by magnets 226. The islands 216 can be moved and configured to achieve a desired flow of dilute pulp through the flow cell 220.

In an alternate, off-line embodiment of the present invention, a pulp sample is manually fed to dilution tank 26 for dilution and dispersion in batch mode. This off-line embodiment also supplies flow cell 50 via gravity or pump, but the overflow at line 60 is preferably recycled back to the dilution tank 26.

The flow cell 50 of FIG. 2A is preferably fabricated from an elongate section of transparent flow tube sandwiched between two dispersion blocks 52a, 52b. Preferably, flow tube 50 is constructed from a transparent plastic or tempered glass material to reduce the likelihood of breakage. To provide leak-free operation, the flow cell 50 is seated in gasketed depressions 54a, 54b in respective blocks 52a, 52b and is held in compression by an over-center, quick-release cam latch (not shown). The quick-release cam latch also enables easy replacement of the flow cell 50 should it become scratched or otherwise degraded to the point that measurement accuracies are affected. A computer controlled, bubble blast system 46 is connected in-line between the pulp sampling/dilution system 20 and imaging/analysis system 70 to provide automatic cleansing of the flow cell 50.

As diluted pulp passes through the flow cell 50, the imaging/analysis system 70 captures images of pulp objects, such as shives, dirt, fines, and individualized fibers, that are positioned within an imaging area 80. As objects pass through the imaging area 80, surfaces of the objects are illuminated by an aperatured, high intensity lighting system shown generally at 62. The imaging/analysis system 70 includes up to four video cameras for capturing images: a primary camera 82, an optional secondary camera 84, an optional third 86, and an optional fourth camera (not shown). In a preferred embodiment, each of the cameras 82-86 are charge coupled device (CCD) cameras providing at least 640×480 image resolution with a shutter capability of up to 1/10,000 of a second. Actual shutter speed used may vary, however, depending on need.

As FIG. 2 illustrates, the lighting system 62 is positioned substantially at ninety degrees, or orthogonal to the focal plane of primary camera 82 so that side scattered light is reflected directly off objects within the flow cell 50 and received by the camera lens 88. Light exiting the lighting system 62 is restricted by slit aperture 102 to a single plane output so that only a relatively narrow cross section (illumination area 80) of the flow cell 50 is illuminated. In a preferred embodiment shown in FIG. 3, lighting system 62 includes a dc, regulated, incandescent light source 104, an infrared filter 105, a fiber optic distribution plate 106 positioned to receive light produced by the dc regulated lamp 104, and a complement of fiber optic cables 107 connected to the distribution plate 106 and terminating at connector 108. The output ends of cables 107 are held in one-dimensional alignment by connector 108, producing a planar output of light that illuminates area 80.

To maximize laminar flow characteristics, the illumination area 80 is positioned near the upstream end of the flow cell 50. Objects entering the flow cell 50 pass through illumination area 80 where they are illuminated by light source 62. Primary camera 82 is focused at a camera plane having a relatively wide depth of field enhanced by use of a telecentric lens, creating a field of view 81 within the illumination area 80 within which fibers and other pulp objects are imaged. Of course, the field of view 81 will differ from that shown in FIG. 2 for different applications. For example, when measuring shives content, the field of view 81 will typically be larger than when measuring fines content. FIG. 4, which illustrates a typical image captured by primary camera 82 when measuring individual fiber characteristics, shows that the camera's field of view 81 is large enough to include several objects within the image, yet small enough to maintain sufficient magnification to enable identification of most objects by simple visual inspection. For example, in the image of FIG. 4 there can be seen, and readily identified, an individual pulp fiber 110, a broken fiber 112, and dirt 114. To enhance parallel light gathering and increase depth of field, primary camera 82 may be equipped with a telecentric lens.

In operation, displayed images are typically scrutinized by system operators, or automatically by the system 10, to determine the image's fitness for computer analysis. Images may contain only partial views of objects, or objects may not have been imaged with sufficient clarity, or perhaps no objects at all were captured in the image. In such cases, the image is discarded and another is taken until an image containing a sought after object having sufficient clarity and profile is obtained. For example, if fiber length and curliness are being sought, then an individual fiber 110 must be captured within the image. Once the desired image is captured, various fiber parameters can then be determined through image analysis.

The output of primary camera 82 on lines 83, being a CCD camera, consists of a plurality of analog voltage signals produced by a plurality of pixels (picture elements) in two-dimensional alignment (640×480) where the voltage level for each signal corresponds an average light level for one pixel of the image. In a preferred embodiment, primary camera 82 outputs signals varying between 0–5 volts. A computer 90 (FIG. 1) receives the output of primary camera 82 on lines 83, processes, and analyzes the signals to determine various properties of objects that have been imaged. For example, when analyzing fiber properties, the computer 90 is programmed to determine fiber length, perimeter, area, and curliness (which indicates the amount and rigor of the refining process).

A functional block diagram of the computer 90 is illustrated in FIG. 5. Processor 140 shown in FIG. 5 represents the necessary software filters, program control, and memory capacity for analyzing and storing images as described herein. The camera outputs on lines 83, 85, and 87 are received by a framegrabber board 130 where the analog signals of the images are converted to digital (8-bit, 0–256 graylevel, proportional to voltage) and held by the framegrabber 130 for display and analysis. The analog-to-digital converter of the framegrabber 130 converts each of the pixel voltages to a digital graylevel value corresponding to the average amount of light received by the pixel. In an 8-bit digital conversion, $2^8$ (256) possible graylevel values are created ranging from the lowest graylevel value of 0 (no light) to 255 (pixel saturated with light).

In a preferred embodiment, framegrabber 130 is an overlay framegrabber (OFG) board manufactured by Instrument Technologies, Inc. which utilizes a Pentium™ 100 mHz processor with PCI interface capability. The digitized image held by framegrabber 130 is processed by motion blur filters residing in processor 140 to eliminate motion blur. The motion blur filter eliminates motion blur from the captured image by extrapolating between odd/even raster scans and then redrawing the image in accordance with the extrapolation result. The filtered image is displayed on the RGB monitor 73 for visual observation and evaluation.

In an alternate embodiment, the motion blur filter is eliminated by utilizing alternate image acquisition equipment similar to the equipment disclosed in U.S. Pat. application Ser. No. 08/738,341, filed Oct. 25, 1996, entitled Measurement of Visual Characteristics of Paper, the entire contents of which are expressly incorporated herein by reference. Briefly, the alternate equipment includes a full-frame array camera such as a Cidtec™, non-standard (e.g., non-RS-170) array camera (512×512), and a PCI BitFlow Raptor board (framegrabber) along with a high speed, timed strobe for object illumination. Use of this equipment combination eliminates the need for a motion blur filter and allows higher flow rates, but substantially increases the cost of the system 10.

As previously discussed, it is preferable to keep only the clearest, brightest images of fibers and other objects for further analysis. If the image displayed on the visual image monitor 72 does not exhibit sufficient object clarity and detail, such as when an object is only partially lit, the image is rejected and another is captured and displayed. Images exhibiting sufficient clarity are provided to the processor 140 for image analysis with the use of software filters. Processor 140 also provides the necessary control of an I/O control board 150 which performs all of the I/O functions for control and operation of the light source 62 through line 146, the dilution system 20 through line 144, and the bubble blast system 46 through line 142.

Image analysis software and image processing algorithms residing in processor 140 are preferably written in Advanced Language for Imaging (ALI) and provide processing of the image based on system graylevel, critical mean graylevel, and various morphology filters. Object parameters produced by the image analysis process, in addition to being displayed on a computer image monitor 71, are automatically saved to archival files and spreadsheet files residing in electronic memory within the processor 140. It should be noted that, although a preferred embodiment of the invention as shown in FIG. 1 utilizes two separate monitors 71, 72 for display of visual and computer images, it will be understood that a single monitor may be used instead. When a single monitor is to be used, it is preferable to incorporate split screen capability so that visual and computer images can be displayed simultaneously.

The analyzed image may be displayed on the computer image monitor 71, or through appropriate user inputs entered by a keyboard 74 or mouse 75 the user may display any number of preformatted graphical displays representing compilations of measured parameters. For example, a graph illustrating the most recent fiber area measurements may be generated by the processor 140 from spreadsheet data and displayed on a monitor 72, 73, as illustrated by the graph of FIG. 6. From further analysis of the FIG. 6 graph, it can be seen that average fiber area is 0.016 mm$^2$. A printer 91 may be attached to the computer 90 for printing measured parameters in hard copy format. Plant personnel can then utilize the graphical information to adjust pulp process variables as necessary. In other words, a graphical illustration of fiber curliness, for example, for the most recent six-hour production period provides plant personnel with valuable feedback and information on how well the pulp production process is performing. Various object parameters are graphically summarized at user defined intervals, and the graphical display on monitor 72 can be changed by the user at any time to display the current state of any measured parameter.

A flow diagram of the image analysis process is illustrated in FIG. 7. As previously described, an image is grabbed (block 160) and displayed (block 162) on a monitor 72, 73. When not using a strobe lighting system, the captured image is filtered to eliminate motion blur (block 164). In analyzing an image, processor 140 compares each pixel of the image to a system threshold graylevel (block 166), such as 140. Pixels that do not meet the threshold are eliminated from the image (block 170). Contiguous pixels meeting the system threshold graylevel are converted to objects (block 172) and each object is then compared to objects within the previous image to determine whether there are any objects that have not moved (block 174). To prevent duplication in the measurements, objects that have not moved during the period of time between consecutive image grabs are eliminated from the image (block 176). For each object remaining, an average pixel value is calculated (block 178) and compared to a critical mean threshold graylevel (block 180), such as 180, to eliminate all but the brightest, or most favorably illuminated objects from the image (blocks 182, 184). If the average pixel value does not meet the established critical mean, the entire object is eliminated from the image. Even partially lit objects are preferably eliminated from the image. In this way, only the brightest, clearest, most visible objects are kept for parameter measurement. Objects meeting the critical mean threshold graylevel are then compared to various size and shape (morphology) filters (block 186) to determine a variety of parameters And information relative to the object that has been imaged, including the type of object (i.e., shive, dirt, fines, or fiber). The size of the object including length, perimeter, area, roundness, and aspect ratio can also be determined by measurement. The measured properties are then stored to archival and spreadsheet files stored in memory (block 188).

To prevent duplicate measurements of objects that have adhered to the inner surface of the flow cell 50, each image is compared to the previous image by generating a two-dimensional plot of each image and then comparing it to a two-dimensional plot of the next succeeding image. Objects within two or more successive images having substantially the same size, shape, and location are assumed to be objects that have adhered to the surface of the flow cell 50 and are ignored. When such a repeat of objects occurs, bubble blast system 46 should be initiated and the flow cell 50 flushed to purge the immobilized objects.

If necessary, a secondary camera 84 may be added to the system 10 to provide extremely accurate measurements of object details such as fiber width. Because of the relatively wide view angle provided by primary camera 82, object details such as fiber width are sometimes difficult to measure with sufficient accuracy. The secondary camera 84 is equipped with a high zoom lens to permit higher magnification of the imaging field, producing a second field of view that is smaller than the primary camera's first field. In this manner, objects captured in an image produced by primary camera 82 are greatly magnified for higher resolution and detail in the image captured by the secondary camera 84. Alternatively, if obtaining a wide field of view image is not important to the user, then the primary camera 82 can be fitted with a high zoom lens to obtain greater object detail and measurement accuracy.

FIG. 8 illustrates a typical image of the end of a fiber as captured by the secondary camera 84. As can be seen, the image of FIG. 8 contains a higher level of fiber detail and resolution than can be seen from the image of FIG. 4, enabling the processor 140 to determine fiber width with great accuracy.

An optional third camera 86 may be added to the system 10 to provide for multiple angle viewing and integration of object measurements, based on alignment probabilities. Images captured by the primary and third cameras 82, 86 are compared, both visually and/or electronically, to enhance viewing angles and measurement accuracies. Images provided by the primary camera 82 can be integrated with images provided by the third camera 86 to produce a three-dimensional hologram of imaged objects. Such three-dimensional imaging is particularly useful for determining fiber curliness, which serves as a useful indicator of over-refining. In other words, curly fibers generally indicate over-refinement during the pulp production process. Such information enables plant personnel to adjust the pulp production process accordingly to reduce fiber curl.

Images captured by secondary camera 84 are output on lines 85 while images captured by the third camera 86 are output on lines 87. The OFG framegrabber 130, which can handle outputs from up to four cameras, receives the second and third camera outputs, digitizes, and displays them as previously described with respect to primary camera images. The images are processed to eliminate motion blur, as previously described, and analyzed in accordance with the FIG. 6 flowchart to determine object parameters.

In operation, computer 90 is programmed for automatic on-line control of the system 10, including pulp sampling and dilution and image capture and processing. Every few minutes the computer 90 opens solenoid valve 24, allowing the release of a small quantity of pulp from pulp line 22 into the dilution tank 26. As the diluted pulp enters the flow cell 50, the computer 90 controls the framegrabber 130 to initiate light source 62 and capture images with one or more of the cameras 82–86. The captured images are processed by the computer 90 as previously described, and the measured properties of pulp objects are stored over time in memory 150, providing an historical database of pulp properties. Plots, or graphical displays illustrating various pulp properties as measured over time are periodically generated and reviewed by machine operators to ascertain the sufficiency of the pulp production process.

As previously discussed, there are many complex and interrelated process variables involved in pulp production. The graphical plots of measured pulp properties versus time provide machine operators with immediate, on-line feedback that can be utilized to adjust the process variables accordingly. For example, if the measured pulp properties indicate an undesirable mixture of hardwood and softwood, machine operators can adjust the hardwood/software ratio at the pulp storage chests until an optimal mixture is indicated by the measured pulp properties. In another example, measured pulp properties are used to control the amount of mechanical refining, or beating imparted to the pulp. If measurements indicate a high percentage of broken fibers or deformed fibers, the extent of mechanical refining should be reduced. On the other hand, if measurements indicate a high number of shives present in the pulp, machine operators will know that the pulp is being underefined and that the amount of mechanical refining should be increased.

It is contemplated, and will be apparent to those skilled in the art from the foregoing specification, drawings, and examples that modifications and/or changes may be made in the embodiments of the invention. Accordingly, it is expressly intended that the foregoing are illustrative of preferred embodiments only, not limiting thereto, and that the true spirit and scope of the present invention be determined by reference to the appended claims.

What is claimed is:

1. A system for determining characteristics of objects having surfaces, including wood fibers, dirt and shives, in wood pulp, the system comprising:

means for diluting the pulp in a liquid to provide a wood pulp slurry having a consistency in the range of from about 0.01 to about 0.001 percent;

a transparent flow cell in flow communication with said means for diluting for receiving the pulp slurry;

means for conducting the pulp slurry into the flow cell;

a light source positioned adjacent said flow cell for radiating light into an illumination area of the cell, wherein upon initiation of said light source light radiated by said light source into the illumination area is reflected off surfaces of said objects to produce scattered light;

a first camera positioned substantially orthogonal to said light source and adjacent said flow cell at a first viewing angle to the illumination area so that upon initiation of said camera it is operable to receive a portion of the scattered light in a first field of view containing light reflected directly from surfaces of said objects, producing a first plurality of video signals corresponding to scattered light received by said first camera;

a framegrabber circuit for initiating said light source and camera, receiving said first plurality of video signals, digitizing said first plurality of video signals to produce a first image having a plurality of pixels in a two-dimensional array, and holding said first image for display and analysis;

a digital data processor for controlling said framegrabber circuit to cause said circuit to initiate said light source and camera and produce said first image, said data processor including means for analyzing said first image to produce a second image containing substantially only objects having predefined sizes and shapes, said processor further including means for analyzing said second image to determine one or more object characteristics;

a display for visually displaying at least said second image; and means for electronically transferring said second image from said data processor to said display.

2. A system in accordance with claim 1, wherein said first camera comprises a charge coupled device camera producing a first matrix of signals corresponding to the two-dimensional array of pixels of the first image, said system further comprising a filter for eliminating motion blur from said first image.

3. A system in accordance with claim 1, wherein said light source comprises a strobed light source, said first camera comprises a full-frame array camera, and said framegrabber circuit comprises a Bitflow Raptor board.

4. A system in accordance with claim 1, wherein said means for analyzing further comprises means for comparing each of said pixels to a threshold value, identifying as objects contiguous pixels that equal or exceed the threshold value, and filtering the objects to eliminate objects that do not meet predefined size and shape criteria to produce said second image.

5. A system in accordance with claim 4, further comprising means for storing said second image, wherein said digital data processor is programmed to store at least said second image in said means for storing.

6. A system in accordance with claim 1, wherein said light source further includes an elongate aperture through which light exits the light source to illuminate objects contained in the illumination area of said flow cell, producing the scattered light.

7. A system in accordance with claim 6, wherein said first camera includes a telecentric lens having a first depth of field greater than the first field of view.

8. A system in accordance with claim 1, wherein said means for diluting further comprises:

a dilution tank;

a valve connected to said conduit for diverting pulp from said conduit into said dilution tank;

means for inputting water to said tank; and means for mixing the water and pulp to produce the dispersed pulp.

9. A system in accordance with claim 1, wherein said light source further comprises:

a dc regulated incandescent light source for producing light;

a fiber optic distribution plate adjacent said light source to receive light produced by said light source;

a plurality of fiber optic cables connected to said distribution plate for transmitting the light received by said distribution plate, producing transmitted light; and a connector for positioning said plurality of fiber optic cables in a one-dimensional alignment to produce a substantially planar beam of light which is projected into the illumination area of the cell to produce the scattered light.

10. A system in accordance with claim 1, further comprising a second camera positioned adjacent said flow cell at a second viewing angle to receive scattered light from a second field of view smaller than said first field of view, said second camera producing a second plurality of video signals corresponding to scattered light received by said second camera, said second plurality of video signals being digitized by said framegrabber circuit to produce a third image having a plurality of pixels in a two-dimensional array, said framegrabber circuit holding said third image for display and analysis, said digital data processor controlling said framegrabber circuit to output the third image for display and analysis, said processor including means for analyzing said third image to produce a fourth image corresponding to only the width of a fiber positioned within said second field of view, said processor including means for analyzing said fourth image to determine fiber width.

11. A system in accordance with claim 10, further comprising a third camera positioned adjacent said flow cell at a third viewing angle to receive scattered light from the first field of view, said third camera producing a third plurality of video signals corresponding to scattered light received by said third camera, said third plurality of video signals being digitized by said framegrabber circuit to produce a fifth image having a plurality of pixels in a two-dimensional array, said framegrabber circuit holding said fifth image for display and analysis, said digital data processor controlling said framegrabber circuit to output the fifth image for display and analysis, said processor including means for analyzing said fifth image to produce a sixth image corresponding to only fibers positioned within said first field of view, analyzing said sixth image to determine one or more fiber characteristics, and comparing said one or more fiber characteristics determined from said sixth image with said one or more fiber characteristics determined from said second image to improve accuracies of said one or more fiber characteristics.

12. A system in accordance with claim 11, wherein said data processor includes a motion blur filter for reducing image blur associated with displaying images on said display.

13. A method for determining characteristics of wood fibers in wood pulp, comprising the steps of:

dispersing wood pulp in a liquid to produce a wood pulp slurry having a consistency in the range of about 0.01 to 0.001 percent, said pulp slurry having objects contained therein, including wood fibers;

conducting the pulp slurry to a transparent flow cell;

illuminating with a light source objects, including wood fibers, contained within an illumination area of said flow cell;

imaging objects positioned within a first field of view of the illumination area at a first substantially orthogonal viewing angle to said light source to produce a first plurality of video signals containing illuminated objects;

digitizing said first plurality of video signals to produce a first image having a plurality of pixels in a two-dimensional array;

analyzing said first image to produce a second image containing only objects having predefined sizes and shapes that are positioned within said first field of view; and analyzing said second image to determine one or more characteristics of objects contained in said second image.

14. The method of claim 13, wherein said one or more characteristics of fibers are selected from the group consisting of fiber length, fiber perimeter, fiber area, and fiber curliness.

15. The method of claim 13, wherein said analyzing step further comprises the steps of:

comparing each of said pixels to a threshold value;

identifying as objects contiguous pixels that equal or exceed the threshold value; and filtering the objects to eliminate objects that do not equate with predefined threshold sizes and shapes of objects.

16. The method of claim 13, further comprising the step of storing at least said second image.

17. The method of claim 13, wherein said dispersing step comprises the steps of:

diverting pulp from a pulp flow conduit into a dilution area;

inputting water to the dilution area; and mixing the water and pulp to produce the pulp slurry.

18. The method of claim 13, further comprising the steps of:

imaging illuminated objects positioned within a second field of view of the illumination area which is smaller than said first field of view to produce a second plurality of video signals containing illuminated objects;

digitizing said second plurality of video signals to produce a third image having a plurality of pixels in a two-dimensional array; and analyzing said third image to produce a fourth image corresponding to only the width of an object positioned within said second field of view.

19. The method of claim 13, further comprising the steps of:

imaging objects positioned within the first field of view at a second substantially orthogonal viewing angle to produce a third plurality of video signals containing illuminated objects;

digitizing said third plurality of video signals to produce a fifth image having a plurality of pixels in a two-dimensional array;

analyzing said fifth image to produce a sixth image containing only objects positioned within said second field of view; and comparing one or more characteristics of fibers contained in the sixth image with said one or more fiber characteristics of the second image to enhance the accuracy of said one or more fiber characteristics.

20. The method of claim 13, further comprising the step of displaying at least said second image.

21. A system for determining characteristics of objects having surfaces, including wood fibers, in wood pulp, the system comprising:

means for dispersing the pulp in a liquid to provide a wood pulp slurry having a consistency in the range of from about 0.01 to 0.001 percent;

a transparent flow cell for receiving the pulp slurry;

means for conducting the pulp slurry into the flow cell;

a light source positioned adjacent said flow cell for radiating light into an illumination area of the cell, wherein light radiated by said light source into the illumination area is scattered at substantially ninety degrees off surfaces of said objects to produce scattered light;

a first camera positioned substantially orthogonal to said light source and adjacent said flow cell at a first viewing angle to the illumination area to receive scattered light from the first field of view, producing a first plurality of video signals corresponding to scattered light received by said first camera;

a second camera adjacent said flow cell at a second viewing angle to the illumination area to receive scattered light from a second field of view smaller than said first field of view, said second camera producing a second plurality of video signals corresponding to scattered light received by said second camera;

a third camera adjacent said flow cell at a third viewing angle to the illumination area to receive scattered light from the first field of view, said third camera producing a third plurality of video signals corresponding to scattered light received by said third camera;

a framegrabber circuit for initiating said light source and cameras, receiving said first, second, and third plurality of video signals, digitizing said first, second, and third plurality of video signals to produce first, second, and third images, respectively, each having a plurality of pixels in two-dimensional alignment, and holding said first, second, and third images for display and analysis;

a digital data processor for controlling said framegrabber circuit to cause said circuit to initiate said light source and cameras and output the first, second, and third images for display and analysis, said data processor including means for analyzing said first, second, and third images to produce fourth, fifth, and sixth images, respectively, said processor including means for analyzing said fourth, fifth, and sixth images to determine one or more object characteristics; and a display for displaying at least images.

22. A method for on-line control of properties of a wood pulp slurry containing objects, including wood fibers, comprising the steps of:

refining wood to produce refined wood pulp having wood pulp characteristics;

dispersing refined wood pulp in a liquid to produce a wood pulp slurry having a consistency in the range of about 0.01 to 0.001 percent, said pulp slurry having objects contained therein, including wood fibers;

conducting the pulp slurry to a transparent flow cell;

illuminating with a light source objects, including wood fibers, contained within an illumination area of said flow cell;

imaging objects positioned within a first field of view of the illumination area at a first substantially orthogonal viewing angle to said light source to produce a first plurality of video signals containing illuminated objects;

digitizing said first plurality of video signals to produce a first image having a plurality of pixels in a two-dimensional array;

analyzing said first image to produce a second image containing only objects having predefined sizes and shapes that are positioned within said first field of view;

analyzing said second image to determine one or more characteristics of objects contained in said second image; and adjusting said refining step in accordance with determined object characteristics to optimize wood pulp characteristics.

* * * * *

UNITED STATES PATENT AND TRADEMARK OFFICE
CERTIFICATE OF CORRECTION

PATENT NO. : 5,786,894
DATED : July 28, 1998
INVENTOR(S) : William R. Shields, et al It is certified that error appears in the above-identified patent and that said Letters Patent is hereby corrected as shown below:

Column 1, line 47, after "depending" insert -- on --

Column 1, line 54, after "fibers" insert -- , --.

Column 1, line 54, after "fibers" delete "and/or".

Column 2, line 13, delete "systems".

Column 4, line 33, delete "The".

Column 4, line 50, after "a" insert -- graphical representation of a --.

Column 4, line 56, delete "Fig. 7" and insert -- Figs. 7A-B --.

Column 4, line 59, after "a" insert -- graphical representation of a --.

Column 6, line 56, delete "88" and insert -- 83 --.

UNITED STATES PATENT AND TRADEMARK OFFICE
CERTIFICATE OF CORRECTION

PATENT NO. : 5,786,894
DATED : July 28, 1998
INVENTOR(S) : William R. Shields, et al It is certified that error appears in the above-identified patent and that said Letters Patent is hereby corrected as shown below:

Column 7, line 43, after "corresponds" insert -- to --.

Column 7, line 65, delete "$28^8$ " and insert -- $2^8$ --.

Column 9, line 11, delete "FIG. 7" and insert -- FIGS. 7A-B --.

Column 10, line 13, delete ",".

Column 12, line 53, delete "10 " and insert -- 1 --.

Signed and Sealed this

Fourth Day of May, 1999

*Attest:*

*Attesting Officer*

Q. TODD DICKINSON

*Acting Commissioner of Patents and Trademarks*